(12) United States Patent
Yang et al.

(10) Patent No.: US 12,685,531 B2
(45) Date of Patent: Jul. 21, 2026

(54) SURGICAL STAPLE CARTRIDGE AND A SURGICAL END EFFECTOR ASSEMBLY WITH BUMPS

(71) Applicant: Cilag GmbH International, Zug (CH)

(72) Inventors: Mengli Yang, Shanghai (CN); Xiangchun Hong, Shanghai (CN); Anil K. Nalagatla, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/851,251

(22) PCT Filed: Apr. 5, 2023

(86) PCT No.: PCT/IB2023/053478
§ 371 (c)(1),
(2) Date: Sep. 26, 2024

(87) PCT Pub. No.: WO2023/194933
PCT Pub. Date: Oct. 12, 2023

(65) Prior Publication Data
US 2025/0255605 A1 Aug. 14, 2025

(30) Foreign Application Priority Data
Apr. 8, 2022 (CN) .......................... 202210369103.X

(51) Int. Cl.
*A61B 17/072* (2006.01)
(52) U.S. Cl.
CPC .. *A61B 17/072* (2013.01); *A61B 2017/07228* (2013.01); *A61B 2017/07257* (2013.01); *A61B 2017/07271* (2013.01)
(58) Field of Classification Search
CPC .................................................... A61B 17/072
See application file for complete search history.

(56) References Cited

U.S. PATENT DOCUMENTS 4,354,628 A * 10/1982 Green .................. A61B 17/072
227/19
4,527,724 A 7/1985 Chow et al.
(Continued)

FOREIGN PATENT DOCUMENTS

CN 102835983 B 8/2016
EP 0537572 A2 4/1993
(Continued)

OTHER PUBLICATIONS

International Search report and Written Opinion dated Jul. 5, 2023, for International Application No. PCT/IB2023/053478, 9 pages.
(Continued)

*Primary Examiner* — Nathaniel C Chukwurah
(74) *Attorney, Agent, or Firm* — FBT Gibbons LLP

(57) ABSTRACT

A surgical staple cartridge and/or a surgical end effector assembly include/includes bumps. The bumps are provided on the surgical staple cartridge and/or a staple anvil portion. The bumps are positioned and sized to limit rotation of the surgical staple cartridge and the staple anvil portion relative to each other in a closed configuration. The bumps define a gap between the surgical staple cartridge and the staple anvil. The gap limits a maximum pressure applied to tissue by the surgical staple cartridge and the staple anvil, and prevents the tissue from being excessively squeezed to flow to area with no staple line coverage or being unevenly squeezed within the area with staple line coverage and thus affecting a tissue sealing quality. A surgical instrument includes the surgical staple cartridge or the surgical end effector assembly.

20 Claims, 9 Drawing Sheets

(56)　　　　　References Cited

U.S. PATENT DOCUMENTS

| | | | |
|---|---|---|---|
| 4,568,009 | A | 2/1986 | Green |
| 4,573,622 | A * | 3/1986 | Green .................. A61B 17/072 227/19 |
| 4,585,153 | A | 4/1986 | Failla |
| 4,715,520 | A | 12/1987 | Roehr et al. |
| 4,805,523 | A | 2/1989 | Stuckey et al. |
| 4,805,823 | A | 2/1989 | Rothfuss |
| 4,848,637 | A | 7/1989 | Pruitt |
| 4,930,503 | A | 6/1990 | Pruitt |
| 5,439,155 | A | 8/1995 | Viola |
| 5,462,215 | A | 10/1995 | Viola et al. |
| 5,547,117 | A * | 8/1996 | Hamblin .............. A61B 17/072 227/176.1 |
| 5,641,111 | A | 6/1997 | Ahrens et al. |
| 5,810,240 | A * | 9/1998 | Robertson ........... A61B 17/072 227/176.1 |
| 5,919,198 | A | 7/1999 | Graves et al. |
| 6,805,273 | B2 | 10/2004 | Bilotti et al. |
| 6,817,508 | B1 | 11/2004 | Racenet et al. |
| 8,328,064 | B2 * | 12/2012 | Racenet ............... A61B 17/115 227/176.1 |
| 11,202,628 | B2 | 12/2021 | Posey et al. |
| 2004/0084505 | A1 | 5/2004 | Bilotti et al. |
| 2005/0139629 | A1 | 6/2005 | Schwemberger et al. |
| 2011/0226837 | A1 | 9/2011 | Baxter, III et al. |
| 2013/0206813 | A1 | 8/2013 | Nalagatla |
| 2015/0119904 | A1 | 4/2015 | Ji et al. |
| 2017/0281177 | A1 | 10/2017 | Harris et al. |
| 2020/0205810 | A1 * | 7/2020 | Posey .................. A61B 17/072 |
| 2020/0205811 | A1 * | 7/2020 | Posey .................. A61B 17/072 |
| 2020/0337699 | A1 | 10/2020 | Rector et al. |
| 2020/0337700 | A1 | 10/2020 | Hontz et al. |
| 2021/0186495 | A1 | 6/2021 | Shelton, IV et al. |
| 2022/0000479 | A1 | 1/2022 | Shelton, IV et al. |
| 2022/0142641 | A1 | 5/2022 | Wang |
| 2024/0225642 | A1 | 7/2024 | Ren et al. |
| 2025/0049436 | A1 | 2/2025 | Wang |
| 2025/0195065 | A1 | 6/2025 | Yang et al. |
| 2025/0204912 | A1 | 6/2025 | Yang et al. |
| 2025/0213248 | A1 | 7/2025 | Zhang et al. |
| 2025/0213250 | A1 | 7/2025 | Ding et al. |
| 2025/0228559 | A1 | 7/2025 | Ding et al. |
| 2025/0255605 | A1 | 8/2025 | Yang et al. |

FOREIGN PATENT DOCUMENTS

| | | |
|---|---|---|
| EP | 0537572 B1 | 6/1999 |
| EP | 1552791 B1 | 6/2009 |
| EP | 1550411 B1 | 7/2009 |
| EP | 3476310 A1 | 5/2019 |
| EP | 3225179 B1 | 4/2020 |
| EP | 3673826 A1 | 7/2020 |
| EP | 3730070 A1 | 10/2020 |
| EP | 3730069 B1 | 7/2023 |
| EP | 3730068 B1 | 9/2023 |
| EP | 3636166 B1 | 3/2024 |
| WO | 2021/168704 A1 | 9/2021 |
| WO | 2021/168726 A1 | 9/2021 |

OTHER PUBLICATIONS

International Search Report and Written Opinion dated Jul. 4, 2023, for International Application No. PCT/IB2023/053467, 9 pages.
International Search Report and Written Opinion dated Jul. 12, 2023, for International Application No. PCT/IB2023/053469, 9 pages.
International Search Report and Written Opinion dated Jul. 21, 2023, for International Application No. PCT/IB2023/053476, 9 pages.
International Search Report and Written Opinion dated Jun. 29, 2023, for International Application No. PCT/IB2023/053477, 10 pages.
International Search Report and Written Opinion dated Jul. 5, 2023, for International Application No. PCT/IB2023/053481, 10 pages.
International Search Report and Written Opinion dated Jul. 14, 2023, for International Application No. PCT/IB2023/053483, 12 pages.

* cited by examiner

10

113

13A

1121

112

111

11

12

SURGICAL STAPLE CARTRIDGE AND A SURGICAL END EFFECTOR ASSEMBLY WITH BUMPS

FIELD

The present disclosure relates to the field of surgical instruments, in particular, to the field of surgical staplers/anastomats.

BACKGROUND

A surgical stapler/anastomat is usually used to deploy staples into tissue for reducing or eliminating tissue bleeding, for example, it is necessary to seal the tissue as the tissue being cut in order to promote healing. A surgical stapler/anastomat (such as a linear stapler/anastomat, a right-angle stapler/anastomat) may comprise an end effector assembly having a staple cartridge portion and a staple anvil portion, wherein the staple cartridge portion comprises a staple cartridge configured to removably store surgical staples therein, and the staple anvil portion comprises staple forming pockets for shaping staples. Such surgical stapler/anastomat generally comprises a closure system that moves one of the staple cartridge and the staple anvil relative to the other.

As described above, the surgical stapler/anastomat may be configured to close the staple cartridge portion and the staple anvil portion of the end effector assembly into a closed configuration, so as to capture tissue between the staple cartridge portion and the staple anvil portion. In the closed configuration, the staple cartridge portion and the staple anvil portion together apply a clamping force to the tissue, so as to hold the tissue between the staple anvil portion and the staple cartridge portion. Then, the staples are driven to be deployed from the staple cartridge and deformed against the staple forming pockets of the staple anvil portion, thereby fixing tissue layers together. The staples are generally deployed in several staple lines to fix the tissue layers together more reliably. The end effector assembly may comprise or not comprise a cutting member which can be advanced between the staple lines, so as to cut the tissue after the tissue layers have been sealed together.

In the existing surgical staplers/anastomats, when the tissue is clamped between the staple cartridge portion and the staple anvil portion, the tissue may move due to an excessive or uneven clamping force, causing the tissue to leave or deviate from the area with staple line coverage, thus resulting that the tissue cannot be properly sealed. Or, an uneven pressure from one end to the other end that may be formed between staple cartridge portion and the staple anvil portion may results in an uneven staple line, thus affecting healing.

Therefore, there is a need for an improved surgical staple cartridge and surgical end effector assembly to eliminate or reduce the foregoing defects.

SUMMARY OF THE DISCLOSURE

The present disclosure provides an improved surgical staple cartridge and surgical end effector assembly, and a surgical instrument with the surgical staple cartridge or the surgical end effector assembly, the surgical instrument may be a linear stapler/anastomat, a right-angle stapler/anastomat and other similar surgical instruments.

In one aspect, the present disclosure provides a surgical staple cartridge comprising a cartridge body, the cartridge body comprising a tissue contact surface and a plurality of staple cavities formed in the cartridge body for seating surgical staples with each staple cavity forming a staple cavity opening in the tissue contact surface. The staple cartridge further comprises a first bump provided on the tissue contact surface and located adjacent to a first end of the cartridge body, wherein the cartridge body further comprises a channel for a retaining pin to pass therethrough, the channel formed in the cartridge body and located adjacent to the first end, the channel forming a channel opening in the tissue contact surface.

According to a preferred embodiment of the present disclosure, the plurality of staple cavities are arranged into a first row of staple cavities and a second row of staple cavities extending along a longitudinal direction of the cartridge body, each staple cavity opening is provided with protruding parts for grasping tissue, the protruding parts partially surround the staple cavity openings.

According to a preferred embodiment of the present disclosure, the first bump comprises a circumferential wall protruding from the tissue contact surface and extending circumferentially and partially around the channel opening, and wherein both ends of the circumferential wall are integrally connected with adjacent two protruding parts via transition sections, respectively.

According to a preferred embodiment of the present disclosure, the transition sections are slope sections.

According to a preferred embodiment of the present disclosure, the transition sections are straight sections or curved sections.

According to a preferred embodiment of the present disclosure, the channel is transversely offset relative to the first row of staple cavities and the second row of staple cavities, such that a common central axis of the channel and the circumferential wall is located laterally outside the first row of staple cavities and the second row of staple cavities.

According to a preferred embodiment of the present disclosure, the first bump comprises a straight portion and an annular portion, the straight portion protrudes from the tissue contact surface and substantially perpendicular to the longitudinal direction of the cartridge body; and the annular portion protrudes from the tissue contact surface and extends circumferentially around an entire periphery of the channel opening, wherein the straight portion and the annular portion are integrally connected with each other, and a height of the straight portion in a direction perpendicular to the tissue contact surface is greater than a height of the annular portion in the direction perpendicular to the tissue contact surface.

According to a preferred embodiment of the present disclosure, the annular portion is integrally connected with adjacent two protruding parts.

According to a preferred embodiment of the present disclosure, the height of the annular portion is equal to the height of the protruding part.

According to a preferred embodiment of the present disclosure, a thickness of the straight portion in the longitudinal direction of the cartridge body gradually decreases away from the tissue contact surface.

According to a preferred embodiment of the present disclosure, the channel is transversely offset relative to the first row of staple cavities and the second row of staple cavities, such that a common central axis of the channel and the annular portion is located laterally outside of the first row of staple cavities and the second row of staple cavities, while the straight portion is generally centered relative to the first row of staple cavities and the second row of staple cavities in the lateral direction.

According to a preferred embodiment of the present disclosure, the surgical staple cartridge further comprises a second bump protruding from the tissue contact surface and located adjacent to a second end of the cartridge body opposite to the first end, and the plurality of staple cavities are located between the first bump and the second bump.

According to a preferred embodiment of the present disclosure, the first bump has a first height in a direction perpendicular to the tissue contact surface, and the second bump has a second height in the direction perpendicular to the tissue contact surface, wherein the first height is greater than or equal to the second height.

In another aspect, the present disclosure provides a surgical end effector assembly, comprising:

a staple cartridge portion comprising the surgical staple cartridge according to the foregoing embodiments;

a staple anvil portion, the staple anvil portion and the staple cartridge portion are configured to form an open configuration and a closed configuration in order to capture tissue therebetween, and the plurality of staple forming pockets for shaping the plurality of surgical staples are formed in the tissue contact surface of the staple anvil portion.

According to a preferred embodiment of the present disclosure, the staple anvil portion comprises a staple anvil portion bump, and the staple anvil portion bump is located adjacent to an end of the staple anvil portion away from the first bump.

According to a preferred embodiment of the present disclosure, the first bump has a first height in a direction perpendicular to the tissue contact surface of the cartridge body, and the staple anvil portion bump has a second height in a direction perpendicular to the tissue contact surface of the staple anvil portion, and wherein the first height is greater than or equal to the second height.

According to a preferred embodiment of the present disclosure, the surgical staple cartridge further comprises a second bump protruding from the tissue contact surface and located adjacent to a second end of the cartridge body opposite to the first end, and the plurality of staple cavities are located between the first bump and the second bump, and wherein the first bump has a first height in a direction perpendicular to the tissue contact surface, and the second bump has a second height in the direction perpendicular to the tissue contact surface.

According to a preferred embodiment of the present disclosure, the staple anvil portion comprises a third bump, the third bump is provided on the tissue contact surface of the staple anvil portion at a position opposite to the second bump, such that the third bump is able to engage the second bump in the closed configuration.

According to a preferred embodiment of the present disclosure, the third bump has a third height in the direction perpendicular to the tissue contact surface of the staple anvil portion, and the first height is greater than or equal to a sum of the second height and the third height.

In a further aspect, the present disclosure provides a surgical instrument. The surgical instrument comprises the surgical staple cartridge according to the foregoing embodiments or a surgical end effector assembly according to the foregoing embodiments.

The surgical staple cartridge provided by the present disclosure has bump features, the bumps are located and sized to define a gap between the surgical staple cartridge and the staple anvil, to limit rotation of the surgical staple cartridge and the staple anvil relative to each other in the closed configuration, and the gap limits a maximum pressure applied to the tissue by the surgical staple cartridge and the staple anvil, and prevents the tissue from being excessively squeezed to flow to area with no staple line coverage or being unevenly squeezed within the area with staple line coverage and thus affecting a tissue sealing quality. In addition, the structure of the bump may also prevent the tissue from flowing into area with no staple line coverage under squeezing, thereby further improving the tissue sealing quality.

BRIEF DESCRIPTION OF THE DRAWINGS

The present disclosure and its features and advantages will be better understood with reference to the following description of exemplary embodiments of the present disclosure in conjunction with the accompanying drawings. In the following description and drawings, similar components are indicated with similar reference signs. The figures are not necessarily drawn to scale, and for the sake of clarity and conciseness, some parts may be omitted, and some figures may be drawn in an exaggerated or sketchy way.

DETAILED DESCRIPTION OF EMBODIMENTS

Next, exemplary embodiments of the present disclosure will be described in detail with reference to the accompanying drawings. Described herein are merely exemplary embodiments in accordance with the present disclosure, and those skilled in the art will envisage other ways to implement the present disclosure on the basis of the exemplary embodiments described herein, which also fall within the scope of the present disclosure.

Figure 1:
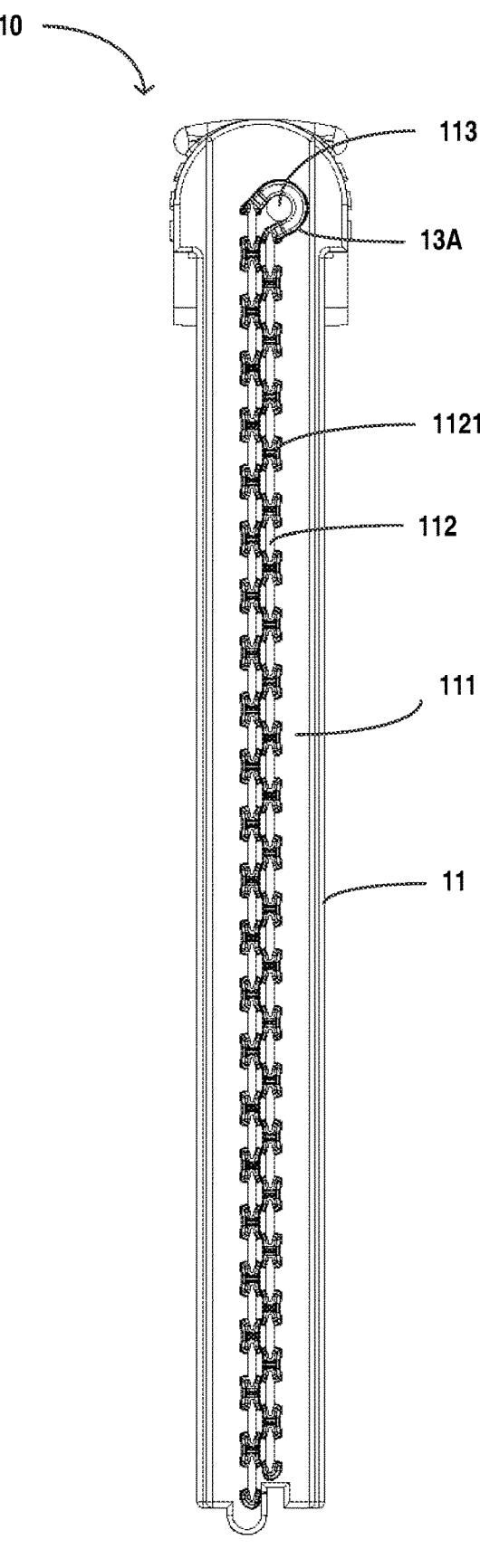
FIG. 1 exemplarily shows a front view of a surgical staple cartridge according to an embodiment of the present disclosure.

FIG. 1 exemplarily shows a front view of a surgical staple cartridge 10 according to an embodiment of the present disclosure. As shown in the figure, the surgical staple cartridge 10 comprises a cartridge body 11, the cartridge body 11 has a tissue contact surface 111 that faces and contacts tissue in use, and a plurality of staple cavities 112 formed within the cartridge body 11, the staple cavities 112 can accommodate surgical staples for suturing the tissue, when fired, the surgical staples are emitted from the staple cavities 112 and penetrate the tissue, and are shaped at a staple anvil portion arranged opposite to the staple cartridge so as to seal the tissue. The cartridge body 11 also comprises a retaining pin channel 113, through which a retaining pin for retaining the tissue will pass and then through the tissue when suturing the tissue. The retaining pin channel 113 is formed in the cartridge body 11 and located adjacent to a first end (shown as an upper end in the figures) of the cartridge body 11, and the channel 113 defines a channel opening in the tissue contact surface 111.

The plurality of staple cavities 112 are arranged in rows, and generally define an area with staple line coverage in a longitudinal direction of the cartridge body. The plurality of staple cavities are arranged into two or more rows (shown as two rows in the figure) of staple cavities extending along the longitudinal direction of the cartridge body, and each staple cavity opening is provided with protruding parts 1121 for assisting in grasping the tissue, and the protruding part 1121 is arranged to partially surround the staple cavity opening.

The surgical staple cartridge 10 further comprises a bump 13A provided on the tissue contact surface 111 and located adjacent to the first end of the cartridge body 11. When the surgical staple cartridge is installed in a surgical stapler, the bump 13A will be located adjacent to an open end of an end effector assembly. The bump 13A defines a gap suitable for the target tissue between the surgical staple cartridge and the staple anvil portion, and limits a maximum pressure applied to the tissue by the surgical staple cartridge and the staple anvil portion, thereby preventing the tissue from being excessively squeezed to flow to area with no staple line coverage or being unevenly squeezed within the area with staple line coverage and thus affecting the tissue sealing quality. At the same time, the bump 13A can also block the tissue along the longitudinal direction, preventing the tissue from flowing into area with no staple line coverage under squeezing, thereby further improving tissue sealing quality.

Figure 2:
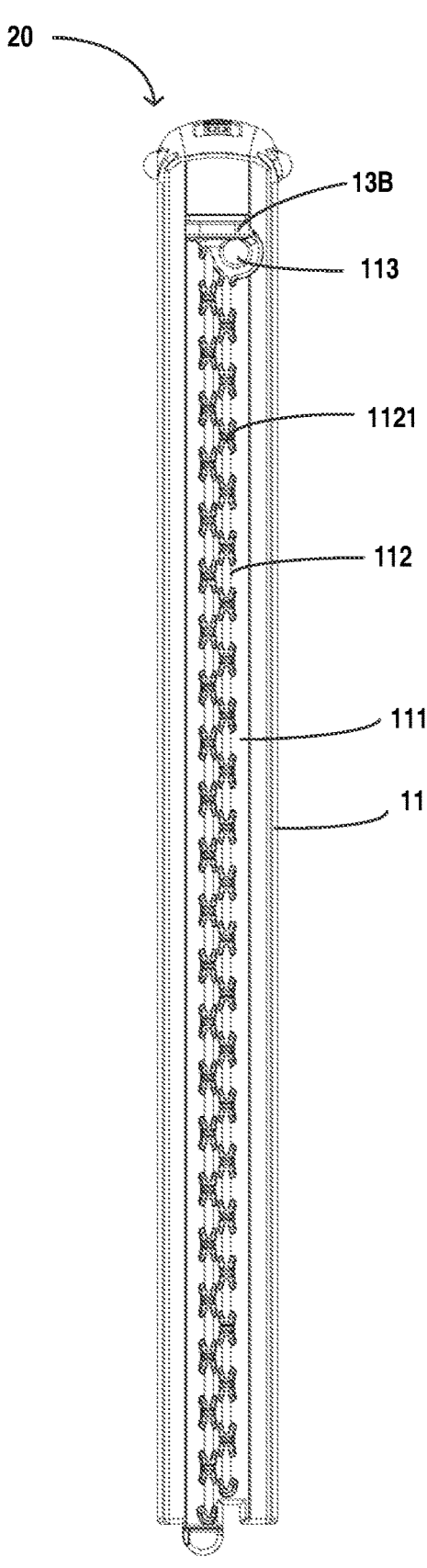
FIG. 2 exemplarily shows a front view of a surgical staple cartridge according to another embodiment of the present disclosure.

FIG. 2 exemplarily shows a front view of a surgical staple cartridge 20 according to another embodiment of the present disclosure. The staple cartridge 20 comprises a bump 13B, and the main difference between the staple cartridge 20 and the staple cartridge 10 is that a specific structure of the bump 13B is different from that of the bump 13A. The position and function of the bump 13B on the cartridge body are substantially the same as those of the bump 13A.

Figure 3:
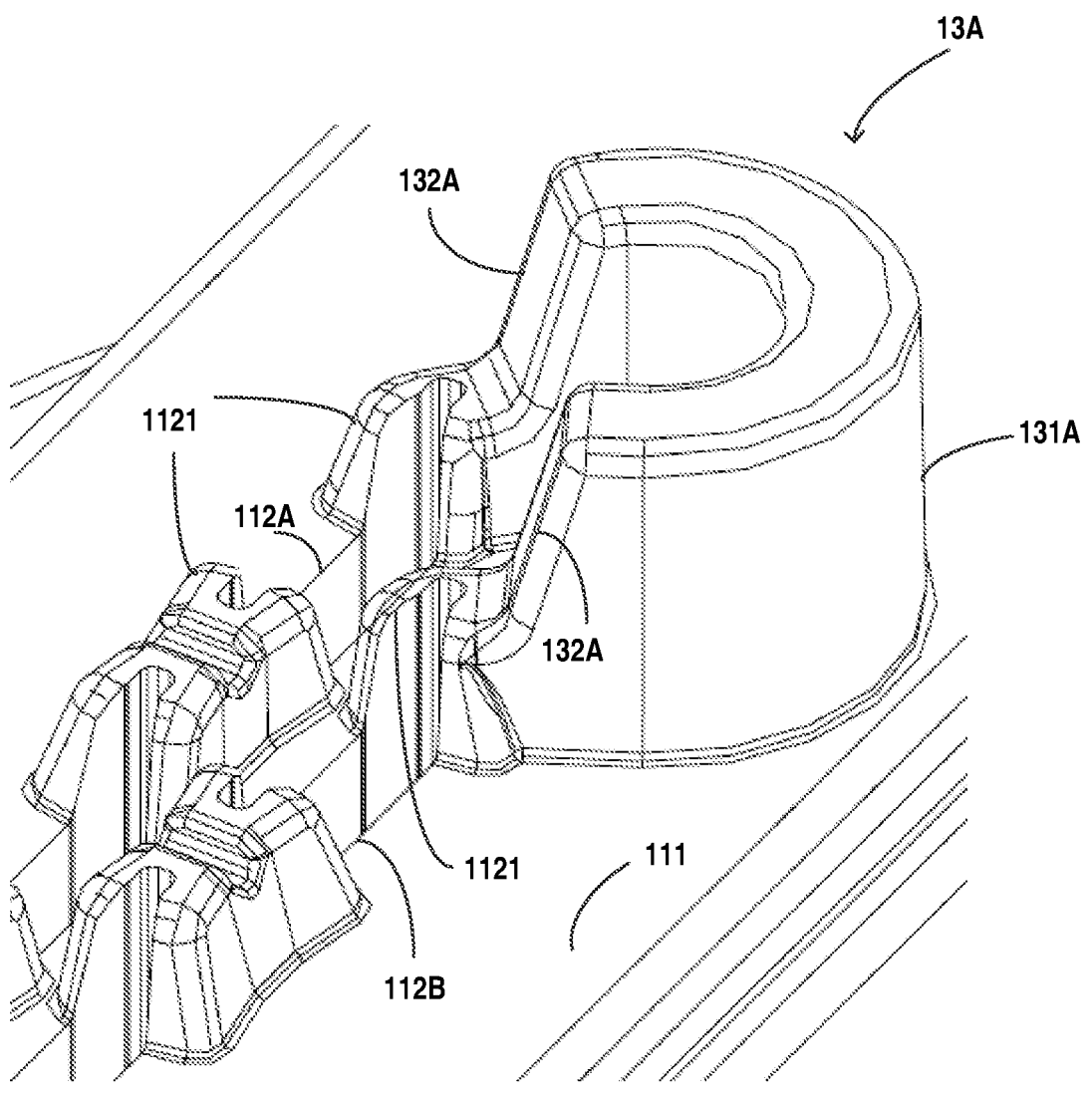
FIG. 3 exemplarily shows a perspective view of a bump of a surgical staple cartridge according to an embodiment of the present disclosure, with the bump located adjacent to a retaining pin channel.
Figure 4:
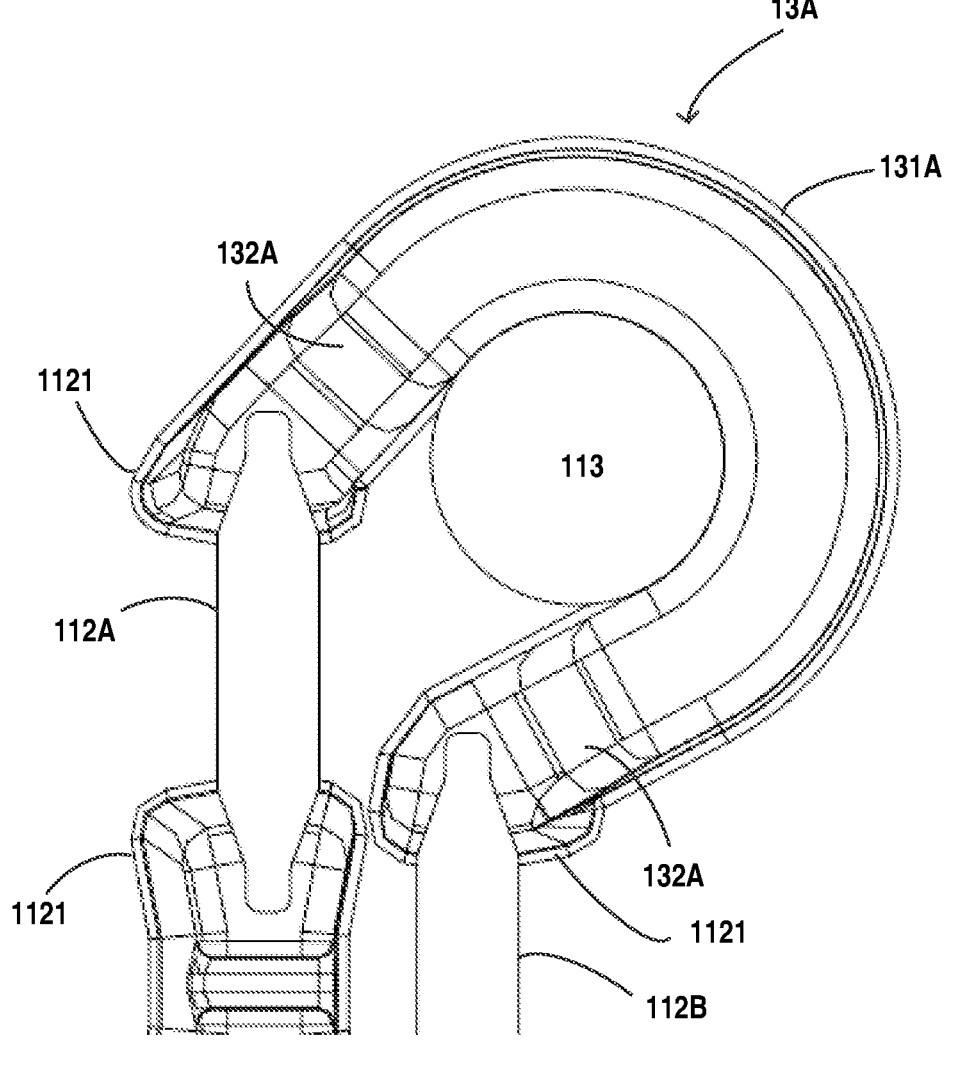
FIG. 4 exemplarily shows a front view of the bump in FIG. 3.

FIG. 3 and FIG. 4 show the specific structure of the bump 13A. As shown in the figures, the retaining pin channel 113 forms the channel opening in the tissue contact surface 111, and the plurality of staple cavities for seating the surgical staples are arranged into two rows of staple cavities 112A and 112B (which may be more than two rows) extending along the longitudinal direction of the cartridge body, each staple cavity defining the staple cavity opening in the tissue contact surface 111, and the surgical staples may be emitted from staple cavity openings when fired. Specifically, the bump 13A is an integral member, which comprises a circumferential wall 131A extending along a circumferential direction of the channel opening of the retaining pin channel 113, the bump 13A partially extends along the circumference of the channel opening, so that the circumferential wall 131A has a C-shape or crescent-shape, of which an opening faces an end region of the two rows of staple cavities. The C-shaped circumferential wall 131A is integrally connected with adjacent two tissue grasp protruding parts 1121 via corresponding transition sections 132A, respectively, so that an end of the area with staple line coverage is jointly closed by the tissue grasp protruding parts 1121 and the bumps 13A, thereby better achieving the technical effect of preventing the tissue from being squeezed out of the area with staple line coverage. Although the transition sections 132A are shown as a slope section, they can also be transition sections with other shapes, such as straight or curved (convex or concave) transition sections.

As further shown in FIG. 4, in order to render the bump 13A closer in the longitudinal direction to the area with staple line coverage defined by the staple cavity opening, the retaining pin channel 113 is transversely offset relative to the two rows of staple cavities, such that a common central axis of the retaining pin channel 113 and the circumferential wall 131A is located laterally outside the two rows of staple cavities.

Figure 5:
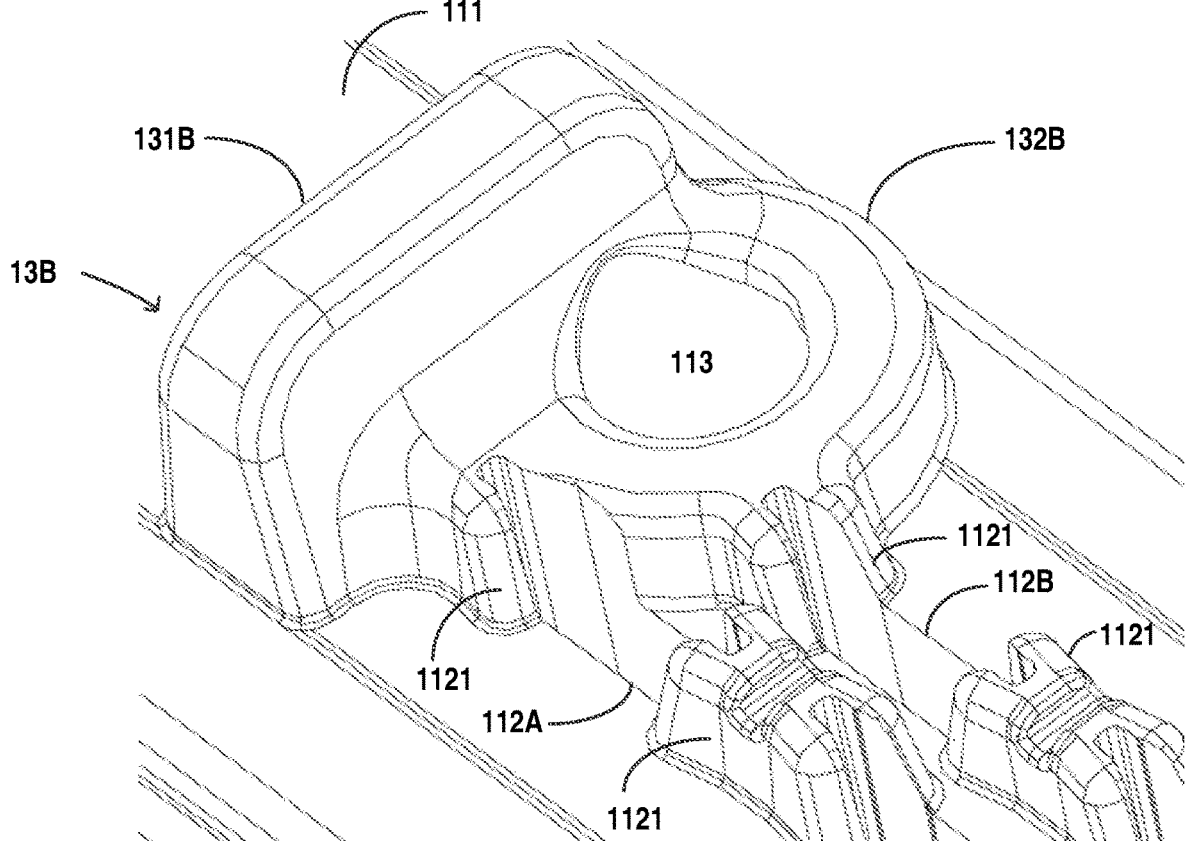
FIG. 5 exemplarily shows a perspective view of a bump of a surgical staple cartridge according to another embodiment of the present disclosure, with the bump located adjacent to a retaining pin channel.
Figure 6:
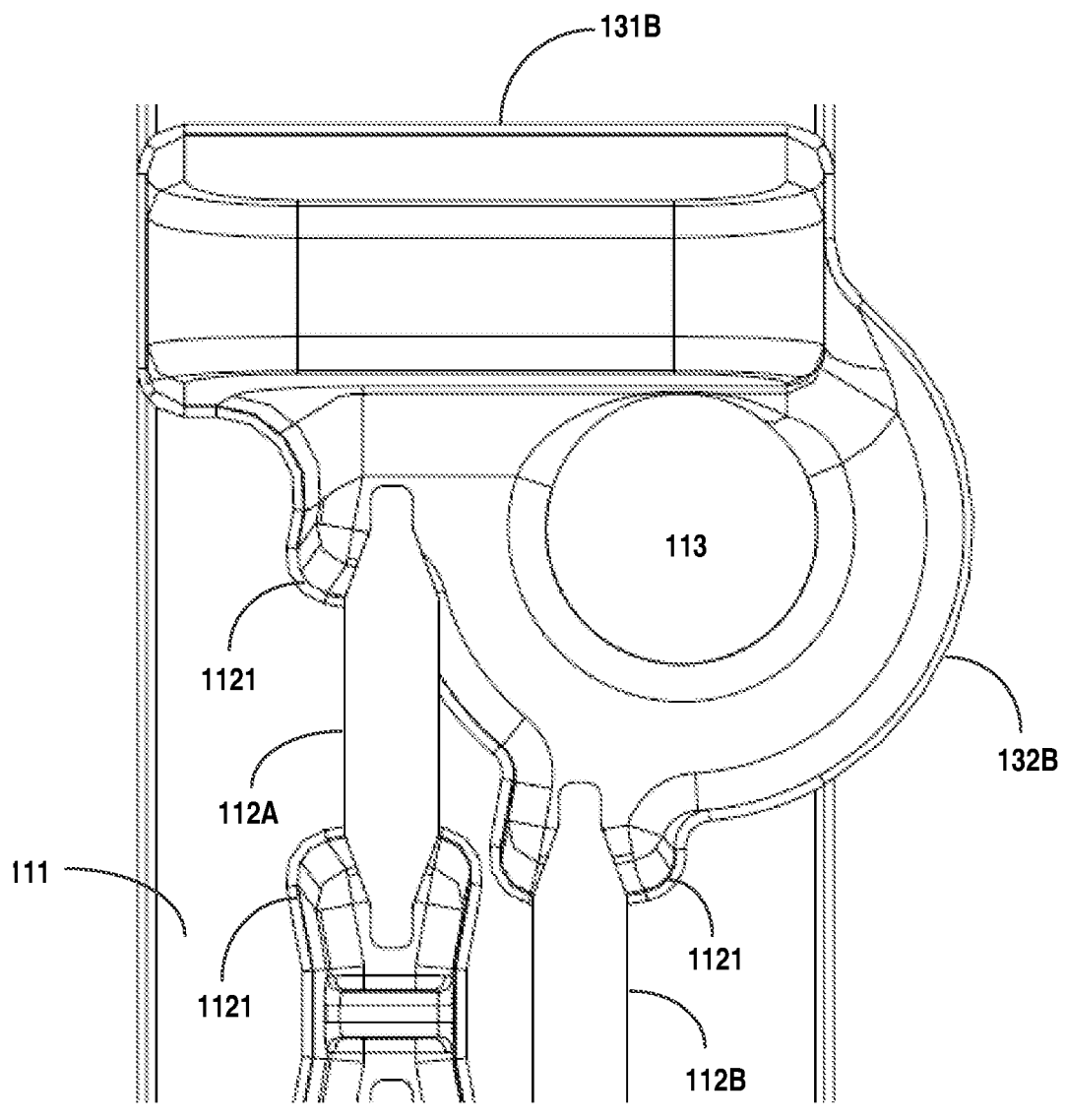
FIG. 6 exemplarily shows a front view of the bump in FIG. 5.

FIG. 5 and FIG. 6 show the specific structure of the bump 13B. Similarly, the retaining pin channel 113 forms the channel opening in the tissue contact surface 111, and the plurality of staple cavities for seating the surgical staples are arranged into two rows of staple cavities extending along the longitudinal direction of the cartridge body, each staple cavity defining the staple cavity opening in the tissue contact surface 111, and the surgical staples may be emitted from the staple cavity openings when fired. Specifically, the bump 13B comprises a straight portion 131B and an annular portion 132B which are integrated with each other. The bump 13B circumferentially surrounds an entire periphery of the channel opening of the retaining pin channel 113. The straight portion 131B protrudes from the tissue contact surface 111 and is generally perpendicular to the longitudinal direction of the cartridge body, thereby preventing the squeezed tissue from leaving the area with staple line coverage along the longitudinal direction, wherein, the height of the straight portion 131B in a direction perpendicular to the tissue contact surface 111 is greater than the height of the annular portion 132B in the direction perpendicular to the tissue contact surface 111. Since that the straight portion 131B and the annular portion 132B circumferentially surround the entire periphery of the channel opening of the retaining pin channel 113, it is also possible to stabilize the retaining pin.

As shown in FIG. 6, the staple cavity opening of an end staple cavity in the two rows of staple cavities 112A and 112B is adjacent to the annular portion 132B, and the annular portion 132B is integrally connected with adjacent two tissue grasp protruding parts 1121, so as to better implement the technical effect of preventing the tissue from being squeezed out of the area with staple line coverage. In addition, the height of the annular portion 132B is equal to the height of the tissue grasp protruding parts 1121.

In a preferred embodiment, the thickness dimension of the straight portion 131B in the longitudinal direction of the cartridge body gradually decreases away from the tissue contact surface 111.

Shown further in FIG. 6, in order to render the bump 13B closer in the longitudinal direction to the area with staple line coverage defined by the staple cavity openings, the retaining pin channel 113 is transversely offset relative to the two rows of staple cavities, such that a common central axis of the retaining pin channel 113 and the annular portion 132B is located laterally outside the two rows of staple cavities, while the straight portion 131B is substantially centered in the lateral direction relative to the two rows of staple cavities.

Figure 7:
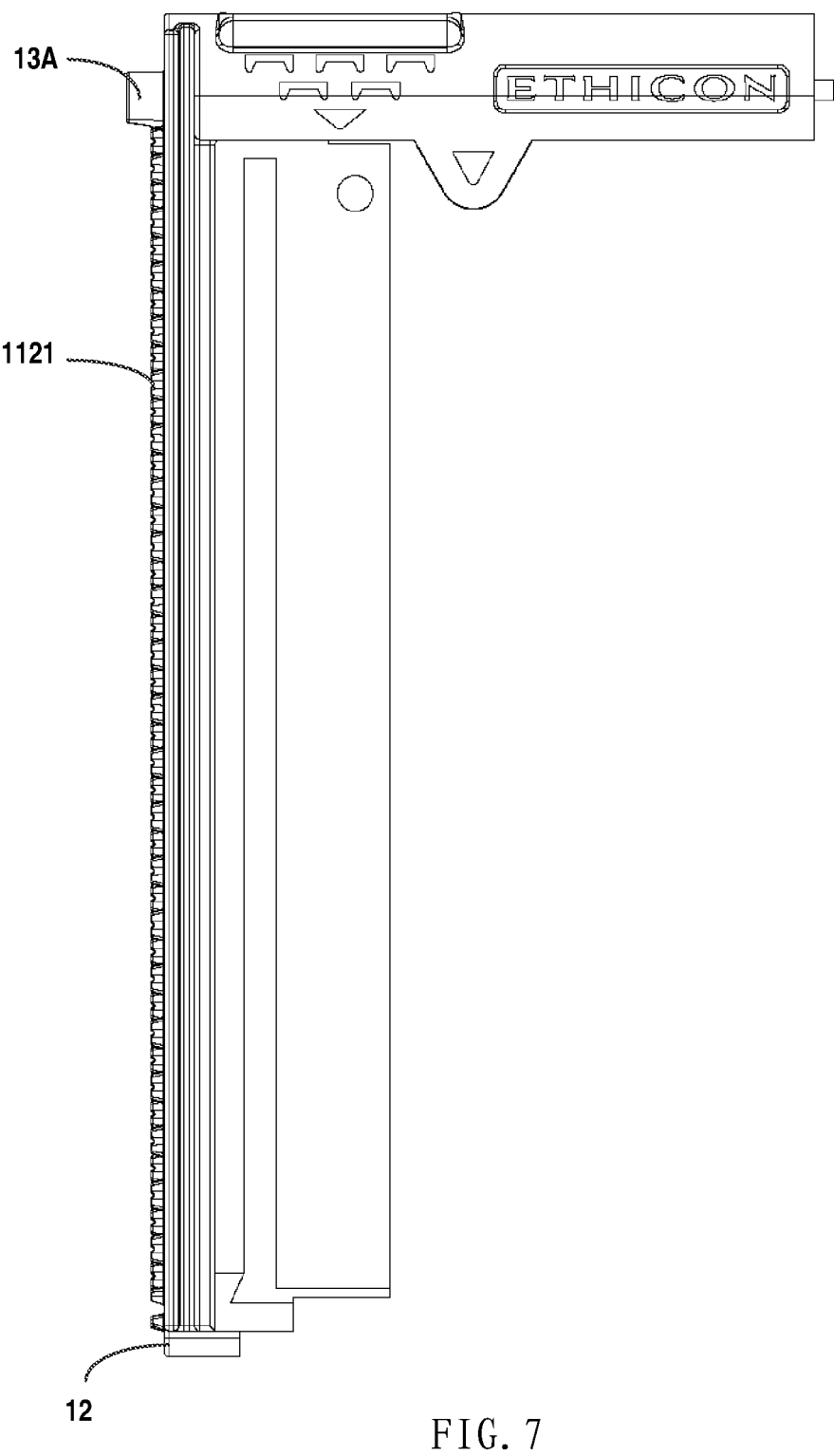
FIG. 7 exemplarily shows a side view of a surgical staple cartridge according to an embodiment of the present disclosure.
Figure 8:
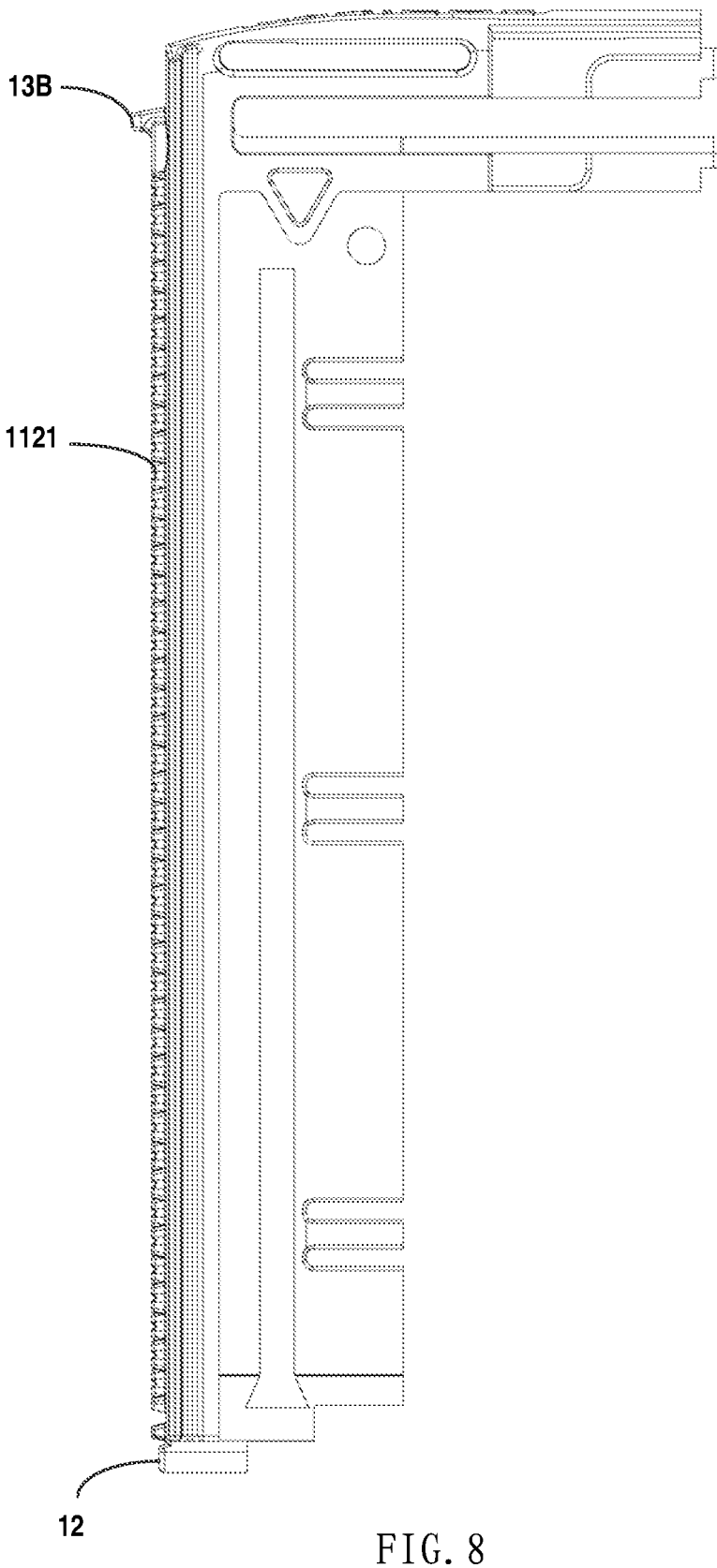
FIG. 8 exemplarily shows a side view of a surgical staple cartridge according to an embodiment of the present disclosure.
Figure 9:
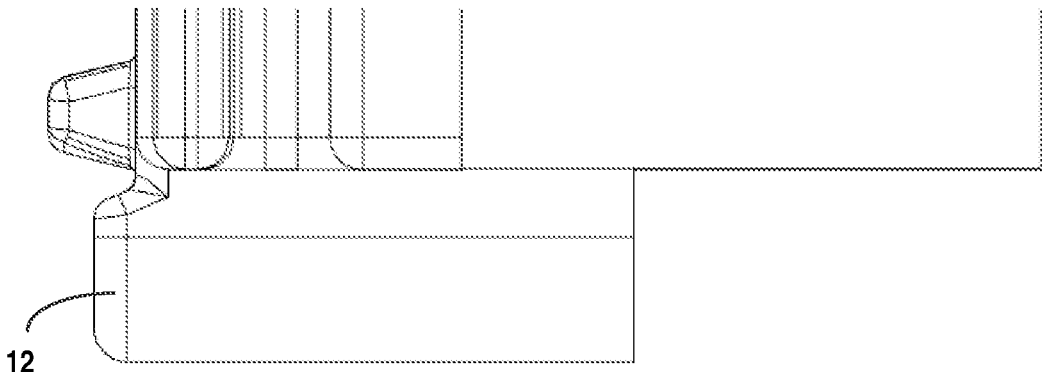
FIG. 9 exemplarily shows a side view of a bump of a surgical staple cartridge according to an embodiment of the present disclosure, with the bump located adjacent to an end away from a retaining pin channel.

Further, the staple cartridge of the present disclosure may further comprise additional bumps. As shown in FIG. 7 and FIG. 8, the bump 12 is located adjacent to a second end of the cartridge body opposite to the first end, and protrudes from the tissue contact surface (as shown in FIG. 9). The plurality of staple cavities is positioned between the bumps 13A/13B and the bump 12. When the surgical staple cartridge is installed in the surgical stapler, the bump 12 will be located adjacent to a closed end of the end effector assembly. The bump 12 cooperates with the bumps 13A/13B to define a gap suitable for the target tissue between the surgical staple cartridge and the staple anvil portion, and at the same time, deformation of the surgical staple cartridge as well as the staple anvil portion in the closed configuration due to a torque generated by a closure plate and an insufficient stiffness of the cartridge body itself can be limited by the height difference. Preferably, the heights of the bumps 13A/13B in the direction perpendicular to the tissue contact surface 111 is greater than the height of the bump 12 in this direction, so as to prevent the staple cartridge from deforming or rotating relative to the staple anvil in the closed configuration.

In another aspect, the present disclosure also provides a surgical end effector assembly, which comprises the staple cartridge portion and the staple anvil portion arranged opposite to the staple cartridge portion, wherein, the staple cartridge portion comprises the surgical staple cartridge described in the previous embodiments. The staple cartridge portion can move relative to the staple anvil portion so as to form an open configuration in which the surgical end effector assembly can receive tissue, and a closed configuration in which the surgical end effector assembly can capture the tissue between the staple cartridge portion and the staple anvil portion, and seal the tissue by firing the staples in the staple cartridge. A plurality of staple forming pockets for forming the surgical staples are formed in the tissue-facing tissue contact surface of the staple anvil portion, the staple anvil portion comprises a staple anvil portion bump which is located adjacent to an end (the closed end of the end effector assembly) of the staple anvil portion away from the bump 13A/13B. When the surgical end effector assembly is closed, the staple anvil portion bump may be engaged with the second end of the staple cartridge (if the staple cartridge does not have the bump 12) or with the bump 12 at the second end. In the case that the staple cartridge has the bump 12, the sum of the heights of the staple anvil portion bump and the bump 12 is less than or equal to the height of the bump 13A/13B; In the case that the staple cartridge only has the bump 13A or 13B and does not have the bump 12, the height of the staple anvil portion bump is less than the height of the bump 13A/13B, which will better limit the deformation of the surgical staple cartridge and the staple anvil portion in the closed configuration due to the torque generated by a closure plate and the insufficient stiffness of the cartridge itself, and at the same time limit the tissue gap, so as to prevent the tissue from being excessively squeezed to move out of the area with staple line coverage or being unevenly squeezed in said area, thus affecting the tissue sealing quality.

In a further aspect, the present disclosure also provides a surgical instrument such as a surgical stapler/anastomat, e.g., a linear stapler/anastomat or a right-angle stapler/anastomat, the surgical instrument comprises the surgical staple cartridge or the surgical end effector assembly according to the above described embodiments.

The scope of protection of the present disclosure is defined only by the claims. References in this specification to "various embodiments", "some embodiments", "one embodiment" or "an embodiment" mean that specific features, structures or characteristics described in conjunction with the embodiments are included in at least one embodiment. Therefore, the phrases "in various embodiments", "in some embodiments", "in one embodiment" or "in an embodiment" and the like in the present specification are not necessarily all referring to the same embodiment. Furthermore, in one or more embodiments, the specific features, structures or characteristics may be combined in any suitable way. Therefore, without conflict, the specific features, structures or characteristics shown or described in conjunction with one embodiment can be fully or partially combined with the features, structures or characteristics of one or more other embodiments, and the resulting modifications and variations are also within the scope of the present disclosure.

We claim:

1. A surgical staple cartridge, comprising:
   a cartridge body, the cartridge body comprising:
      a tissue contact surface,
      a plurality of staple cavities formed in the cartridge body for seating a plurality of surgical staples, wherein each staple cavity forms a staple cavity opening in the tissue contact surface, and
      a channel for a retaining pin to pass therethrough, the channel formed in the cartridge body and located adjacent to a first end of the cartridge body, the channel forming a channel opening in the tissue contact surface; and
   a first bump provided on the tissue contact surface and located adjacent to the first end, wherein at least a portion of the channel is within at least a portion of the first bump.

2. The surgical staple cartridge according to claim 1, wherein the plurality of staple cavities are arranged into a first row of staple cavities and a second row of staple cavities extending along a longitudinal direction of the cartridge body, each staple cavity opening is provided with protruding parts for grasping tissue, the protruding parts partially surround the staple cavity openings.

3. The surgical staple cartridge according to claim 2, wherein the first bump comprises a circumferential wall protruding from the tissue contact surface and extending circumferentially and partially around the channel opening, and wherein both ends of the circumferential wall are integrally connected with adjacent two protruding parts via transition sections, respectively.

4. The surgical staple cartridge according to claim 3, wherein the transition sections are slope sections.

5. The surgical staple cartridge according to claim 3, wherein the transition sections are straight sections or curved sections.

6. The surgical staple cartridge according to claim 3, wherein the channel is transversely offset relative to the first row of staple cavities and the second row of staple cavities, such that a common central axis of the channel and the circumferential wall is located laterally outside the first row of staple cavities and the second row of staple cavities.

7. The surgical staple cartridge according to claim 2, wherein the first bump comprises:
   a straight portion protruding from the tissue contact surface and substantially perpendicular to the longitudinal direction of the cartridge body,
   an annular portion protruding from the tissue contact surface and extending circumferentially around an entire periphery of the channel opening,
   wherein the straight portion and the annular portion are integrally connected with each other, and
   wherein a height of the straight portion in a direction perpendicular to the tissue contact surface is greater than a height of the annular portion in the direction perpendicular to the tissue contact surface.

8. The surgical staple cartridge according to claim 7, wherein the annular portion is integrally connected with two adjacent protruding parts.

9. The surgical staple cartridge according to claim 7, wherein the height of the annular portion is equal to the height of an adjacent protruding part.

10. The surgical staple cartridge according to claim 7, wherein a thickness of the straight portion in the longitudinal direction of the cartridge body gradually decreases away from the tissue contact surface.

11. The surgical staple cartridge according to claim 7, wherein the channel is transversely offset relative to the first row of staple cavities and the second row of staple cavities, such that a common central axis of the channel and the annular portion is located laterally outside of the first row of staple cavities and the second row of staple cavities, while the straight portion is generally centered relative to the first row of staple cavities and the second row of staple cavities in the lateral direction.

12. The surgical staple cartridge according to claim 1, wherein the surgical staple cartridge further comprises a second bump protruding from the tissue contact surface and located adjacent to a second end of the cartridge body opposite to the first end, and the plurality of staple cavities are located between the first bump and the second bump.

13. The surgical staple cartridge according to claim 12, wherein the first bump has a first height in a direction perpendicular to the tissue contact surface, and the second bump has a second height in the direction perpendicular to the tissue contact surface, wherein the first height is greater than or equal to the second height.

14. A surgical staple cartridge, comprising:
a cartridge body, the cartridge body comprising:
    a tissue contact surface,
    a plurality of staple cavities formed in the cartridge body for seating a plurality of surgical staples, wherein each staple cavity forms a staple cavity opening in the tissue contact surface, and
    a channel for a retaining pin to pass therethrough, the channel formed in the cartridge body and located adjacent to a first end of the cartridge body, the channel forming a channel opening in the tissue contact surface; and
a protrusion provided on the tissue contact surface and located adjacent to the first end, wherein the protrusion comprises:

a straight portion protruding from the tissue contact surface and substantially perpendicular to a longitudinal direction of the cartridge body,
    an annular portion protruding from the tissue contact surface and extending circumferentially around a periphery of the channel opening.

15. The surgical staple cartridge according to claim 14, wherein the plurality of staple cavities are arranged into a first row of staple cavities and a second row of staple cavities extending along the longitudinal direction of the cartridge body, each staple cavity opening is provided with protruding parts for grasping tissue, the protruding parts partially surround the staple cavity openings.

16. The surgical staple cartridge according to claim 15, wherein the annular portion comprises a circumferential wall protruding from the tissue contact surface and extending circumferentially and partially around the channel opening, and wherein both ends of the circumferential wall are integrally connected with adjacent two protruding parts via transition sections, respectively.

17. The surgical staple cartridge according to claim 16, wherein the transition sections are slope sections.

18. The surgical staple cartridge according to claim 16, wherein the channel is transversely offset relative to the first row of staple cavities and the second row of staple cavities, such that a common central axis of the channel and the circumferential wall is located laterally outside the first row of staple cavities and the second row of staple cavities.

19. The surgical staple cartridge according to claim 14,
wherein the straight portion and the annular portion are integrally connected with each other, and
wherein a height of the straight portion in a direction perpendicular to the tissue contact surface is greater than a height of the annular portion in the direction perpendicular to the tissue contact surface.

20. A surgical staple cartridge, comprising:
a cartridge body, the cartridge body comprising:
    a tissue contact surface,
    a plurality of staple cavities formed in the cartridge body for seating a plurality of surgical staples, wherein each staple cavity forms a staple cavity opening in the tissue contact surface, and
    an opening for receiving a retaining pin, the opening being formed in the cartridge body and located adjacent to a first end of the cartridge body; and
a protrusion provided on the tissue contact surface and located adjacent to the first end, wherein the opening is formed within the protrusion.

\* \* \* \* \*